US010322258B2

(12) United States Patent
Shin

(10) Patent No.: US 10,322,258 B2
(45) Date of Patent: Jun. 18, 2019

(54) ANION PERFUME MACHINE IN WHICH THROTTLING AND SHOCK ABSORPTION WATER BLOCKING SHEET AND OSCILLATOR GENERATING INCLINED VIBRATION WAVES ARE CONFIGURED

(71) Applicant: KEEPYOUNG TECHNOLOGY TAIWAN LIMITED COMPANY, Taipei (TW)

(72) Inventor: Fu-Zong Shin, Taipei (TW)

(73) Assignee: KEEPYOUNG TECHNOLOGY TAIWAN LIMITED COMPANY, Taipei (TW)

( * ) Notice: Subject to any disclaimer, the term of this patent is extended or adjusted under 35 U.S.C. 154(b) by 54 days.

(21) Appl. No.: 15/591,036

(22) Filed: May 9, 2017

(65) Prior Publication Data

US 2018/0326174 A1   Nov. 15, 2018

(51) Int. Cl.
| | | |
|---|---|---|
| *A61M 21/00* | (2006.01) | |
| *A61M 11/00* | (2006.01) | |
| *B05B 17/06* | (2006.01) | |
| *A61H 33/14* | (2006.01) | |

(52) U.S. Cl.
CPC .......... *A61M 21/00* (2013.01); *A61M 11/005* (2013.01); *B05B 17/0607* (2013.01); *A61H 2033/141* (2013.01); *A61M 2021/0016* (2013.01); *A61M 2205/42* (2013.01)

(58) Field of Classification Search
CPC .......... A61M 21/00; A61M 2021/0016; A61M 2205/42; A61M 11/005; A61H 33/14; A61H 2033/141; B05B 17/06–0692; B05B 17/0615; B05B 17/0623; B05B 17/0607; A61L 9/22; A61L 2/025; A61L 9/16; A61L 9/145; A61L 2209/132; A61L 9/122; A61L 9/12; A01M 1/205
USPC .......................... 239/102.1, 102.2, 4, 589.1
See application file for complete search history.

(56) References Cited

U.S. PATENT DOCUMENTS

| | | | | |
|---|---|---|---|---|
| 9,078,938 | B2 * | 7/2015 | Hsiao | ........................ A61L 9/14 |
| 9,155,846 | B2 * | 10/2015 | Kern | .................... A61M 11/005 |

* cited by examiner

*Primary Examiner* — Jason J Boeckmann
*Assistant Examiner* — Juan C Barrera
(74) *Attorney, Agent, or Firm* — Leong C. Lei

(57) ABSTRACT

An anion perfume machine in which a throttling and shock absorption water blocking sheet and oscillator generating inclined vibration waves are configured, wherein the water blocking sheet is made of soft silicone material and assuming a cross body with four claws, a round petal is adapted to connect the two adjacent claws to each other, a center of the cross body configured with a barbed hook is exactly in engagement with a through hole of a cross rib configured on a center of a throttle cover; an inclined vibration guide unit is lodged in a oscillator accommodation room configured on a bottom of a vibration wave conduction cup; the oscillation unit is constituted by a silicone seat, thereby generating inclined vibration waves, allowing a large number of upward inclined atomized spouts to be sprayed on the essence oil water cup and flow upward along a wall of a cup.

2 Claims, 7 Drawing Sheets

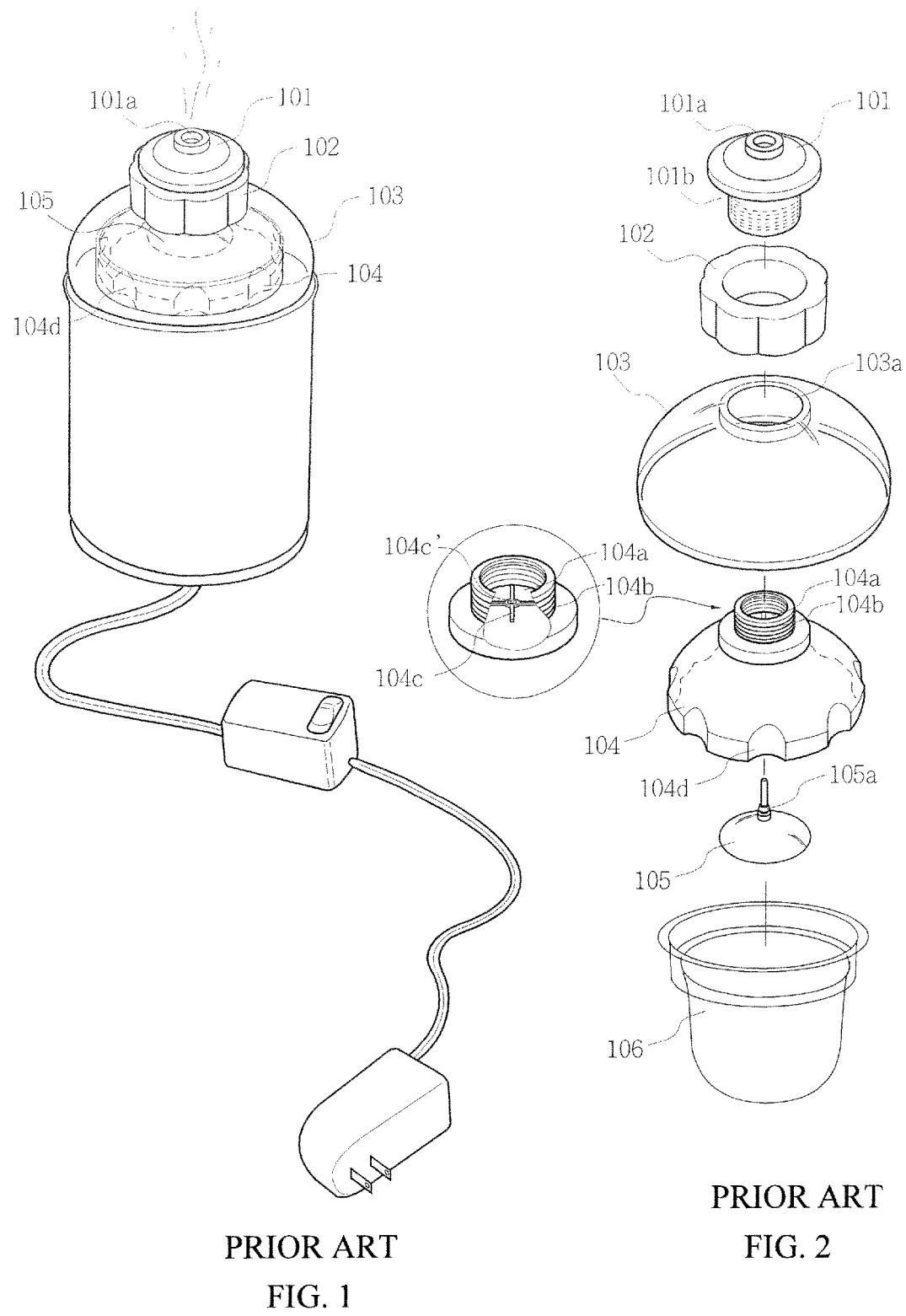
PRIOR ART
FIG. 1
PRIOR ART
FIG. 2

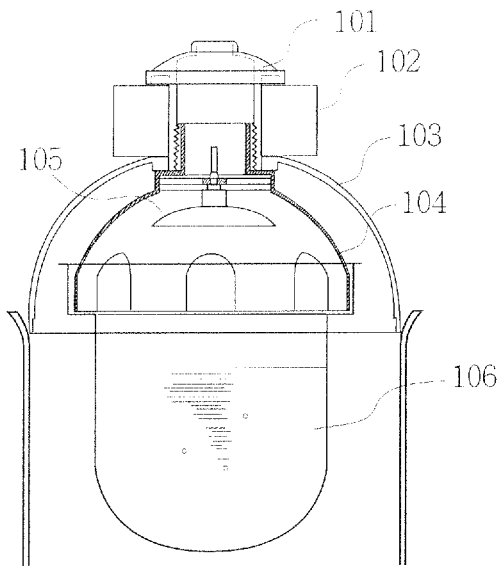
PRIOR ART
FIG. 3
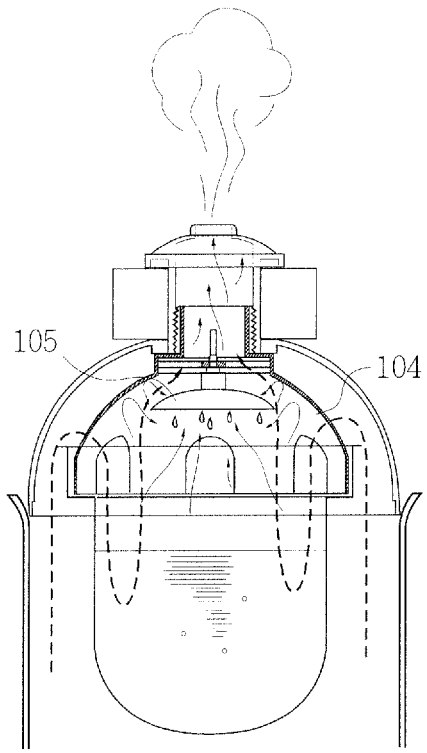
PRIOR ART
FIG. 4

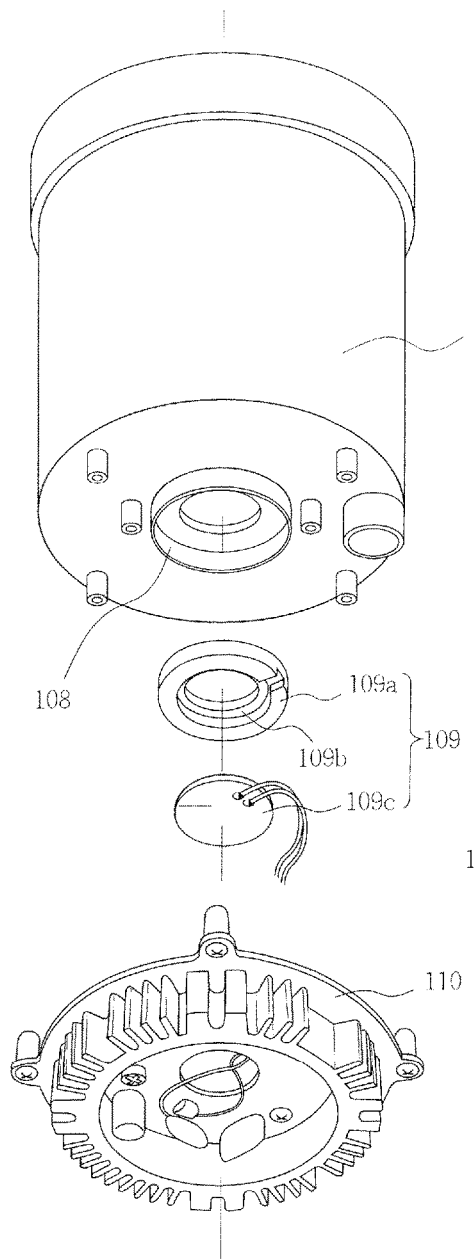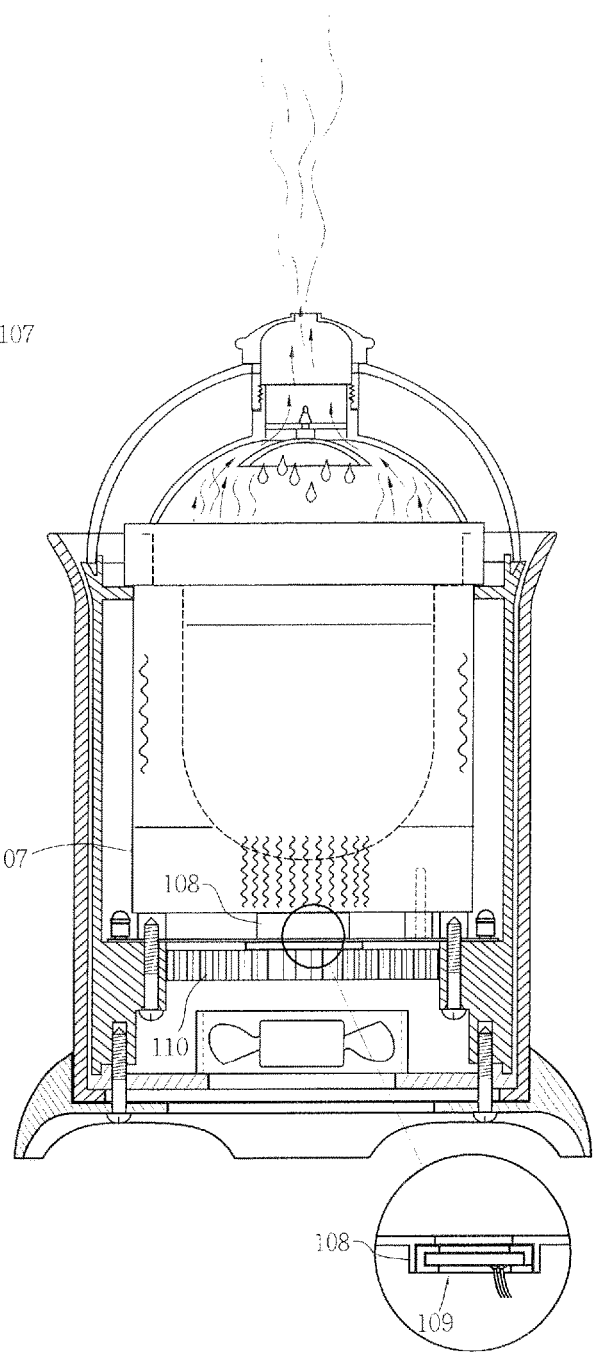
PRIOR ART
FIG. 5A
PRIOR ART
FIG. 5B

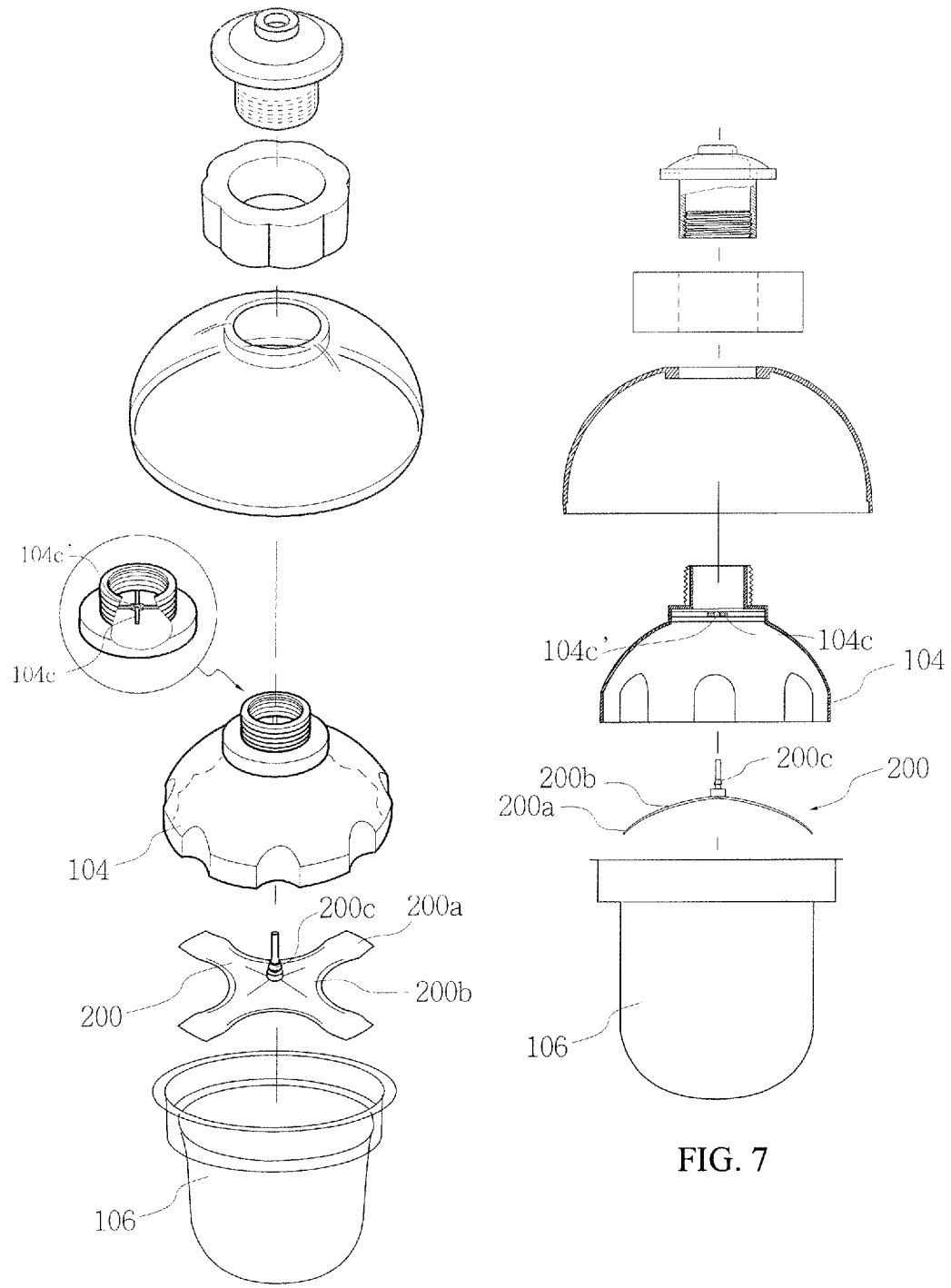
FIG. 6
FIG. 7

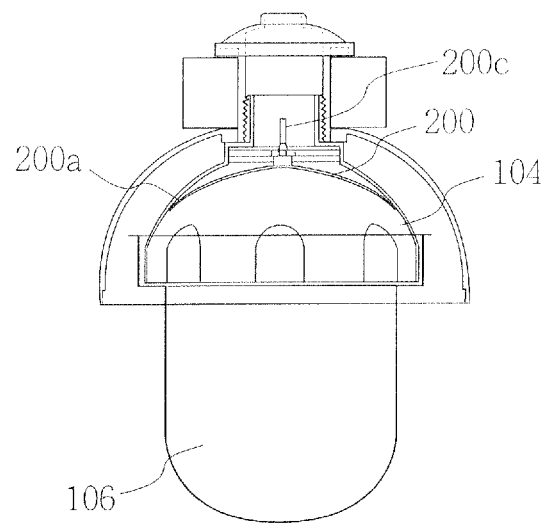
FIG. 8
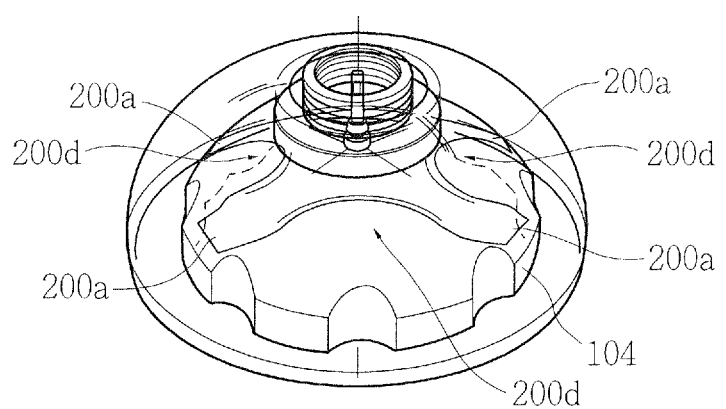
FIG. 9

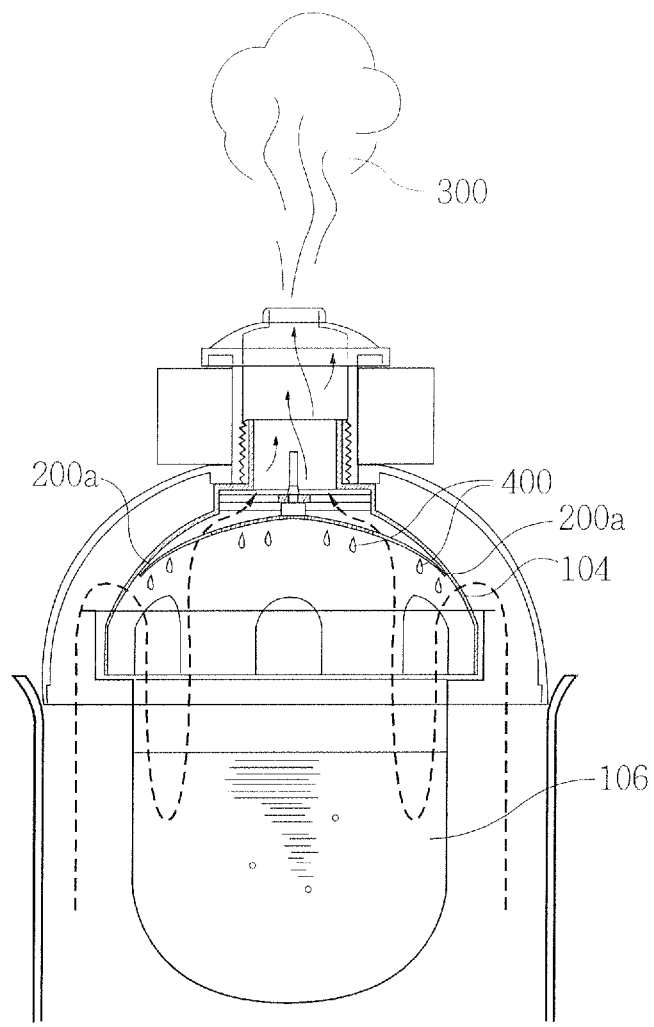
FIG. 10

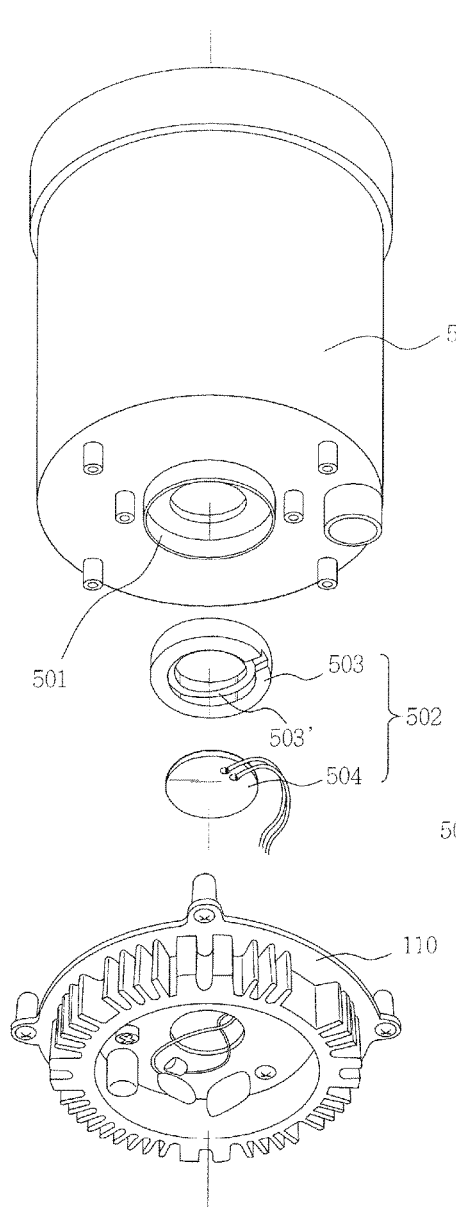
FIG. 11
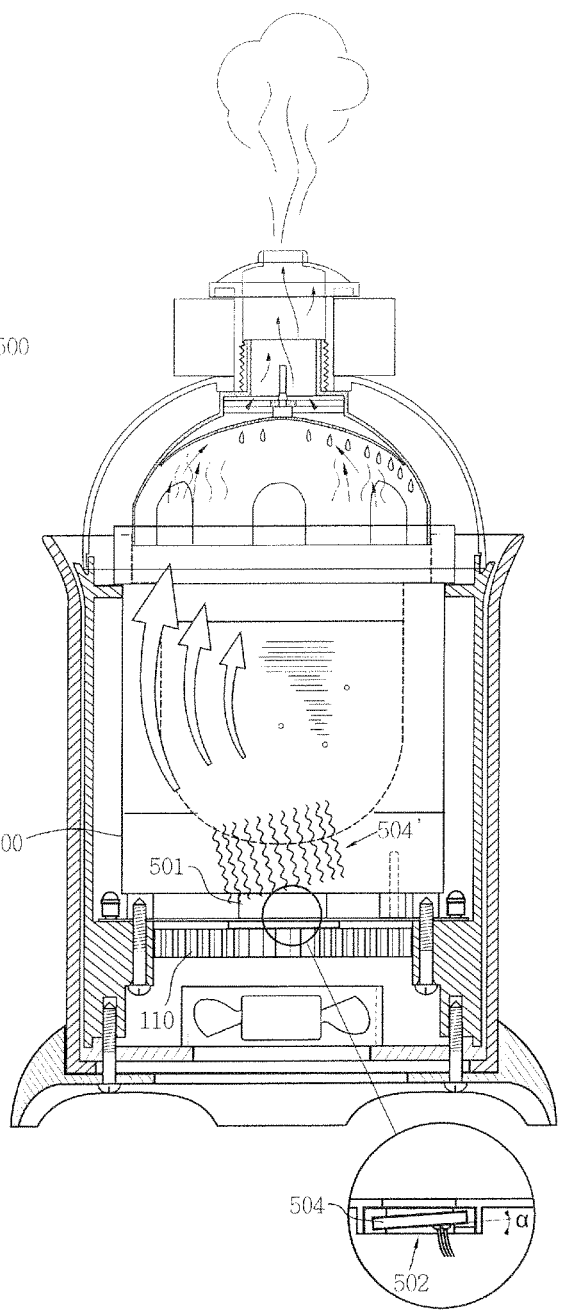
FIG. 12

ANION PERFUME MACHINE IN WHICH THROTTLING AND SHOCK ABSORPTION WATER BLOCKING SHEET AND OSCILLATOR GENERATING INCLINED VIBRATION WAVES ARE CONFIGURED

(a) TECHNICAL FIELD OF THE INVENTION

The present invention relates to an anion perfume machine, and more particularly to an anion perfume machine in which a throttling and shock absorption water blocking sheet and oscillator generating inclined vibration waves are configured

(b) DESCRIPTION OF THE PRIOR ART

Aromatherapy have been discussed for a long time, and many media such as Reader's digest have reported its evolution and application development; in the examples cited in these reports, there still has doubt whether regular medical treatment can be replaced with aromatherapy, but the positive evaluation is still given. Moreover, whether aromatherapy can have covalence effect to the human body is not so important; as long as the appropriate essential oils are chosen to float aroma in the indoor environment to build pleasant fragrance and soothing environment, it is enough. To people, the uncomfortableness will be lessened, the things can be done well, and EQ for emotional management can be improved; it can be said that there are many benefits.

Conventionally, anion perfume machines float essence oils in the air by means of for example, heating (candle/plug-in), isopropyl alcohol aromatherapy method, and micro-oxygen containing aromatherapy method, which might cause explosion after heating, and generate overlarge fragrance particles or ozone and other factors harmful to the environment such that such kinds of machines are not suggested by experts.

A new supersonic aromatherapy, which uses electricity to generate shock waves to oscillate quickly mixture into which essence oil is mixed, is developed recently, such method is safest because of no heating and a best method to accelerate, refine and waft essence oil. However, supersonic perfume machines to which the supersonic aromatherapy is applied still have disadvantages.

Referring to FIGS. 1 and 2, a conventional anion essence oil perfume machine mainly includes a nozzle 101, annular magnet 102, spherical upper cover 103, throttle cover 104, water blocking sheet 105 and inner cup 106, where the nozzle 101 is a cap-typed tube, on upper side of which a through hole 101a is configured, and the inner edge of the tube is configured with inner threads 101b exactly in engagement with an engagement portion 104b projected from the upper edge of the throttle cover 104; the throttle cover 104 is a hemispherical body, the peripheral of which is configured semicircular through holes 104, and the upper side of which is configured with guide holes 104a, a cross rib 104c and through hole 104c', where the through hole 104c' is exactly in engagement with a barbed nail 105a configured on the upper side of the disk-shaped water blocking sheet 105 thereby to fix the barbed nail 10. Further, the spherical upper cover 103 is a hemispherical cover, on the upper edge of which a circular hole 103a is configured. Next, referring to FIG. 3, all the components mentioned above including the nozzle 101, annular magnet 102, spherical upper cover 103, throttle cover 104, water blocking sheet 105 and inner cup 106 can be combined and engaged with one another.

Referring to FIG. 4, essence oil anion smoke generated when an anion perfume machine is in operation will pass through throttle cover 104. At this time, the water blocking sheet 105 originally for adjustment and diversion causes water droplets to be gathered on the center thereof and then drop, which causes upward airflow to be disordered, resulting in unsmooth air output so that smoke cannot be expelled smoothly immediately to make the machine heat easily and even break down. In addition, the water drops drop back to the cup after gathered, producing drip noise; especially at midnight, the noise will affect sleep quality, not allowing peaceful sleep.

Furthermore, referring to FIGS. 5A and 5B, an oscillation unit 109 is lodged in an accommodation room 108 configured on the bottom of a vibration wave conduction cup 107 of the machine body, where the oscillation unit 109 is constituted by a silicone seat 109a with an annular inner groove 109b in which an oscillator 109c is lodged. With the action of an oscillator circuit 110, the resonance action generated by the vibration waves of the oscillator 109 causes the machine body to generate long time low frequency vibration sound to affect sleep quality, which is not significant deficiency but has a room to be improved.

SUMMARY OF THE INVENTION

The object of the present invention is to provide an anion perfume machine in which a throttling and shock absorption water blocking sheet and oscillator generating inclined vibration waves are configured, reducing water drop noise and the vibration sound of a machine body.

The present invention proposes an anion perfume machine in which a throttling and shock absorption water blocking sheet and oscillator generating inclined vibration waves are configured, wherein the water blocking sheet is made of soft silicone material and assuming a cross body with four claws, a round petal is adapted to connect the two adjacent claws to each other, a center of the cross body configured with a barbed hook is exactly in engagement with a through hole of a cross rib configured on a center of a throttle cover; whereby, atomized essence oil water molecules smoke is diverted upward, and excess condensate water drops are allowed to be guided back into a water cup along the claws; whereby, original noisy vibration waves are spread effectively and uniformly to an inner wall of a throttle cover through the vibration guide action of the claws; an inclined vibration guide unit is lodged in a oscillator accommodation room configured on a bottom of a vibration wave conduction cup; the oscillation unit is constituted by a silicone seat, thereby generating inclined vibration waves, allowing a large number of upward inclined atomized spouts to be sprayed on one side of the essence oil water cup and flow upward along a wall of a cup, capable of effectively reducing the back titration phenomena and oscillation resonance generated by the atomized spout turbulence; at the same time, the throttling, diversion and shock absorption of the water blocking sheet is operated in coordination with to generate a powerful guidance effect, allowing the smoke having essence oil anions to be guided out fast and powerfully, generating an optimized atomization waft, and reducing the back titration due to water vapor and drops, thereby preventing the overheat of the machine body, extending the life of the components of the machine body, achieving the throttling and shock absorption, and allowing the quiet operation of the machine body at midnight.

BRIEF DESCRIPTION OF THE DRAWINGS

FIG. 1 is a perspective view of a conventional anion perfume machine;

FIG. 2 is an exploded view of the conventional anion perfume machine;

FIG. 3 is a side view of the conventional anion perfume machine;

FIG. 4 is a schematic view of the conventional anion perfume machine upon operation;

FIG. 5A is an exploded view of the conventional oscillator;

FIG. 5B is a schematic view of the convention oscillator upon operation;

FIG. 6 is an exploded view of an anion perfume machine of the present invention;

FIG. 7 is an exploded schematic view of the anion perfume machine of the present invention;

FIG. 8 is a side view of the anion perfume machine of the present invention;

FIG. 9 is a perspective view of a cross body with four claws of the anion perfume machine of the present invention;

FIG. 10 is a schematic view of the anion perfume machine of the present invention upon operation;

FIG. 11 is an exploded view of an oscillator obliquely vibrating structure according to the present invention; and FIG. 12 is a schematic view of the oscillator obliquely vibrating structure according to the present invention upon operation.

DETAILED DESCRIPTION OF THE PREFERRED EMBODIMENTS

Referring to FIGS. 6 to 8, in an anion perfume machine of the present invention, a water blocking sheet 200 is made from soft silicone and formed into a cross body having four claws 200a, each adjacent pair of which is connected by a round petal 200b, and a barbed hook 200c, which can be exactly in engagement with a through hole 104c' of a cross rib 104c configured on the center of a throttle cover 104, is configured on the center of the water blocking sheet 200.

Referring to FIG. 9, each claw 200a is bent at the tip thereof after assembly, capable of attached uniformly to the inner wall of the throttle cover 104, forming a four-curved petals passage 200d. Next, referring to FIG. 10 too, atomized essence oil water molecules smoke 300 is diverted upward, and excess condensate water drops are allowed to be guided back into the cup 106 along the claws 200a. Whereby, the original noisy vibration waves are spread effectively and uniformly to the inner wall of the throttle cover 104 through the vibration guide action of the claws 200c. Thus, the smoke having essence oil anions cam be guided out fast and powerfully, thereby generating an optimized atomization drift, avoiding obstacle caused from moistures and droplets, prevention the overheating of the machine body, and extending the life of the components of the machine body, and noisy vibration waves are spread effectively and uniformly to the inner wall of the throttle cover 104 through the vibration guide action of the claws 200c, allowing effective throttling and a quite machine body operation.

Referring to FIGS. 11 and 12, a oscillation unit 502 is lodged in a oscillator accommodation room 501 configured on the bottom of a vibration wave conduction cup 500, where the oscillation unit 502 is constituted by a silicone seat 503 in which is configured an inclined annular inner groove 503', in which an oscillator 504 can be exactly lodged, allowing the oscillator 504 to be inclined an angle α. With the action of a oscillator circuit 110, inclined vibration waves 504' generated from the oscillator 504, as FIG. 11 shows, allows a large number of n atomized spouts to be sprayed on one side of essence oil water cup and flow upward along the wall of the cup, capable of effectively reducing the back titration phenomena and oscillation resonance generated by the atomized water column turbulence. At the same time, the throttling, diversion and shock absorption of the water blocking sheet is operated in coordination with to generate a powerful guidance effect, allowing the smoke having essence oil anions to be guided out fast and powerfully, generating an optimized atomization waft, and reducing the back titration due to water vapor and drops, thereby preventing the overheat of the machine body, extending the life of the components of the machine body, achieving the throttling and shock absorption, and allowing the quiet operation of the machine body at midnight.

I claim:

1. An anion perfume machine in which a throttling and shock absorption water blocking sheet and an oscillator generating inclined vibration waves are configured, wherein said water blocking sheet is made of soft silicone material and assuming a cross body with four claws, a round petal is adapted to connect said two adjacent claws to each other, a center of said cross body configured with a barbed hook is exactly in engagement with a through hole of a cross rib configured on a center of a throttle cover; whereby, atomized essence oil water molecules smoke is diverted upward, and excess condensate water drops are allowed to be guided back into a water cup along said claws; whereby, original noisy vibration waves are spread effectively and uniformly to an inner wall of said throttle cover through the vibration guide action of said claws; an oscillation unit is lodged in an oscillator accommodation room configured on a bottom of a vibration wave conduction cup, said oscillation unit is constituted by a silicone seat having an inclined annular inner groove exactly capable of lodging-in of said oscillator, allowing said oscillator to have an inclined angle a after being lodged in, with action of an oscillator circuit, inclined vibration waves generated from said oscillator, capable of effectively reducing back titration phenomena and oscillation resonance generated by atomized spout turbulence.

2. The machine according to claim 1, wherein a tip of each said claw of said cross body is bent after the assembly thereof, said claws are attached uniformly to an inner wall of said throttle cover, forming a four curved petals passage; when said machine body is in operation, smoke with atomized essence oil water molecules is diverted upward effectively, and original machine body noise vibration waves can be scattered and guided effectively uniformly to said inner wall of said throttle cover through a shock guide action of said claws.

* * * * *